United States Patent [19]
Dudar et al.

[11] Patent Number: 5,411,499
[45] Date of Patent: May 2, 1995

[54] NEEDLELESS VIAL ACCESS DEVICE

[75] Inventors: Thomas E. Dudar, Palatine; Peter L. Graham, Gurnee; Steven C. Jepson, Palatine, all of Ill.

[73] Assignee: Baxter International Inc., Deerfield, Ill.

[21] Appl. No.: 737,735

[22] Filed: Jul. 30, 1991

Related U.S. Application Data

[63] Continuation-in-part of Ser. No. 147,414, Jan. 25, 1988, abandoned.

[51] Int. Cl.⁶ .............................................. A61M 37/00
[52] U.S. Cl. ........................................ 604/411; 604/88
[58] Field of Search ........................... 604/411–415, 604/200–206, 87, 88, 283, 166, 164; 215/247; 606/184, 185

[56] References Cited

U.S. PATENT DOCUMENTS

| | | | |
|---|---|---|---|
| 2,102,704 | 12/1937 | Hein | 604/206 |
| 3,826,260 | 7/1974 | Killinger | |
| 3,995,630 | 12/1976 | van der Veerdonk | 604/88 |
| 4,153,057 | 5/1979 | Kobel | |
| 4,244,364 | 1/1981 | Grushkin | |
| 4,328,802 | 5/1982 | Curley et al. | |
| 4,410,321 | 10/1983 | Pearson et al. | |
| 4,589,879 | 5/1986 | Pearson | |
| 4,624,667 | 11/1986 | Rutnarak | 604/88 |
| 4,638,809 | 1/1987 | Kuperus | 604/87 |
| 4,994,029 | 2/1991 | Rohrbough | 604/88 |
| 5,053,014 | 10/1991 | Van Heugtien | 604/205 |

FOREIGN PATENT DOCUMENTS

| | | |
|---|---|---|
| 1171578 | 1/1902 | France . |
| 0843744 | 8/1960 | United Kingdom . |
| 0927020 | 5/1963 | United Kingdom . |
| 0127781 | 12/1984 | WIPO . |
| 0395758 | 11/1990 | WIPO . |

Primary Examiner—Stephen C. Pellegrino
Assistant Examiner—William Lewis
Attorney, Agent, or Firm—Amy L. H. Rockwell; Paul E. Schaafsma; Paul C. Flattery

[57] ABSTRACT

A cannula assembly adapted to pierce a solid or unslit closure is disclosed and includes a blunt cannula and a piercing member held in cooperation with or contained within the flow channel of the cannula. Generally, the piercing member includes a tip capable of piercing an unslit stopper or closure and a means to temporarily retain the piercing member from the cannula and prevent inadvertent disengagement of the piercing member from the blunt cannula.

37 Claims, 8 Drawing Sheets

NEEDLELESS VIAL ACCESS DEVICE

CROSS-REFERENCE TO RELATED APPLICATION

This application is a continuation-in-part application of the commonly assigned U.S. patent application Ser. No. 07/147,414, filed Jan. 25, 1988, abandoned.

FIELD OF THE INVENTION

The invention generally pertains to coupling systems usable to transfer materials from one flow conduit to another. More particularly, the invention pertains to two-part coupling members with a first part including a pre-slit septum and a second part including a blunt cannula. The pre-slit septum slidable receives the blunt cannula to effect the coupling. The systems have particular applicability in the medical field for handling medications and body fluids. The present invention relates generally to a structure for piercing a barrier and placing both sides of the barrier in fluid communication. More particularly, the present invention relates to a cannula assembly adapted for use with stoppers used as closures in drug vials.

BACKGROUND OF THE INVENTION

In the medical field, injection sites usable with pointed cannulae have long been known. For example, such sites can be formed with a housing having a fluid flow path therein. A septum is positioned in the housing closing the fluid flow path.

A pointed cannula can be forced through the septum into fluid flow communication with the flow path in the site housing. Known injection sites usable with a piercing cannula can be physically damaged by repetitive piercing caused by the sharp cannula. This damage, known as coring or laceration, can result in subsequent leakage.

Further, a large number of drugs are packaged in well known glass or plastic drug bottles or vials having rubber-like stoppers. Similar to injection sites, the stoppers on the drug vials are pierceable by a needle or cannula having a sharpened tip when secured to a syringe assembly of a well-known construction. Typically, the needle is brought to a point on one side of the needle wall by a bevel structure so that the needle tip is quite sharp. Drug vials are also subject to coring by such needles. Particulate matter can subsequently be generated and injected into the patient or otherwise contaminate the content of the vial.

Due to problems associated with infectious agents, personnel using such pointed cannulae or needles do so with great care. Notwithstanding careful and prudent practice, from time to time, accidents do occur and individuals using such pointed cannulae accidentally "stick" themselves.

In an effort to overcome some of these difficulties, devices known as "dispensing pins" can be used to penetrate the stopper of drug vials. Such dispensing pins are typically a sharp spike cannula and can employ a check valve in an effort to prevent gross fluid leakage. On the opposing end of the cannula is a standard luer fitment typically closed off, when not in use, by a cap. These dispensing pins tend to disengage from the vial stopper so that some leakage may occur.

Disclosed in pending U.S. Application Ser. No. 07/425,790, filed Oct. 23, 1989, a pre-slit injection site coupled with a component to adapt the site to standard drug vials has been developed to address these same difficulties. Primarily developed for use with multi-dose vials, such an adapter can be lockingly engaged with a drug vial, thereby permitting the usage of a blunt cannula rather than a sharp cannula or needle. However, this adapter may not be a cost efficient device when used with single-dose drug vials.

SUMMARY OF THE INVENTION

In accordance with the present invention, a cannula assembly adapted to pierce a solid or unslit closure, such as a stopper on a standard drug vial, is provided. The cannula assembly includes a blunt cannula which may be of one of the several designs previously disclosed in related pending applications, and a piercing member which can be held by or contained within the flow channel of, the cannula. Generally, the piercing member includes a tip having a sharpened or spike point capable of piercing an unslit stopper or closure, a shaft extending from the tip and a means to release the piercing member from the cannula while preventing inadvertent disengagement of the piercing member and the cannula. Attached to a receiver, such as a standard syringe, the cannula assembly is inserted through the vial stopper and into the vial so that the vial fluid can be infused into the receiver. After infusion, the cannula assembly is withdrawn from the vial with the piercing member being contained within and disposed with the vial. Used in this manner, the cannula assembly allows the medical professional to access a standard drug vial with minimal exposure to a sharpened piercing member and is left with a blunt cannula to conclude the drug administration procedure to a patient.

Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF A PREFERRED EMBODIMENT

Figure 1:
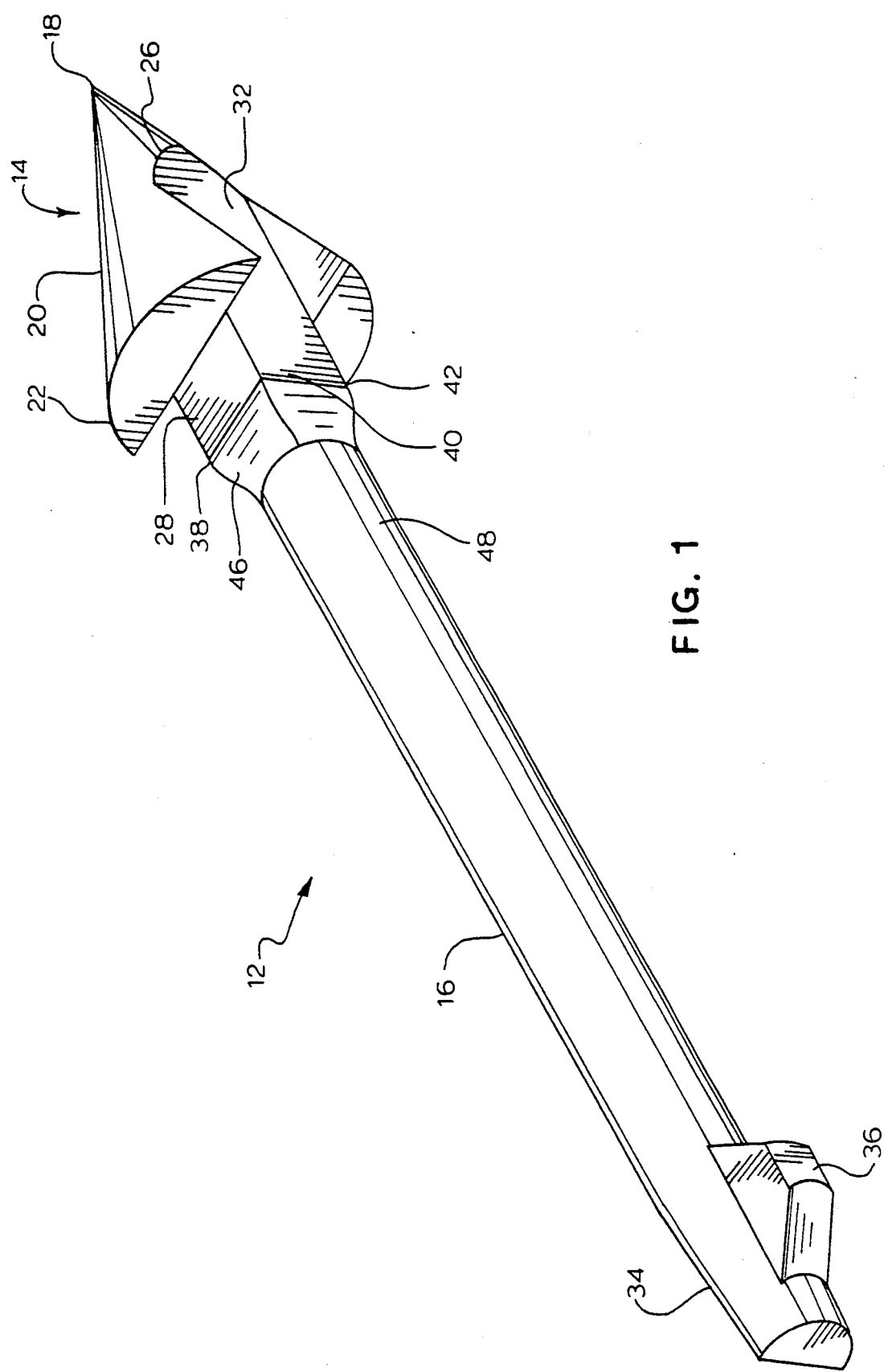
FIG. 1 is a perspective view of the preferred piercing device.
Figure 2:
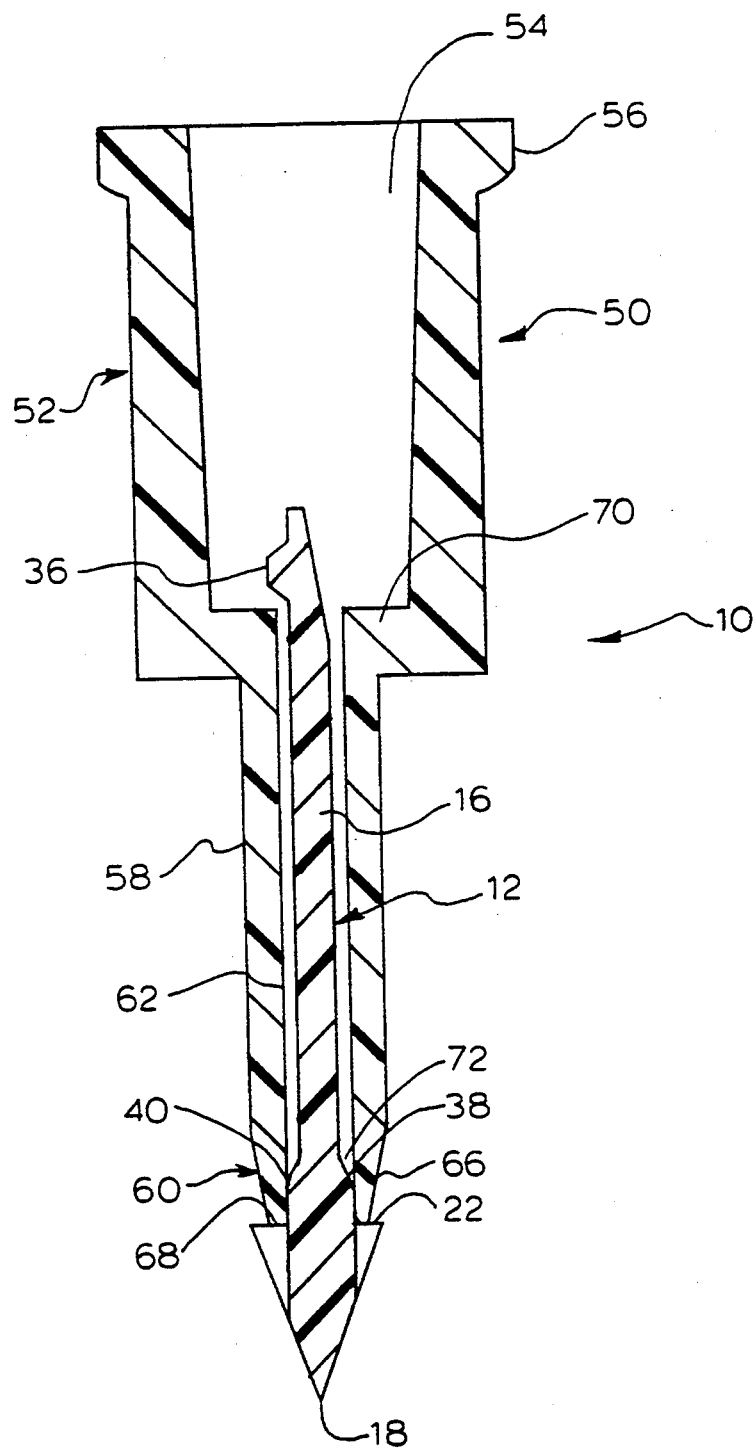
FIG. 2 is a cross-sectional view of the preferred piercing device as contained in the cannula assembly.

The preferred embodiment of the piercing member 12 of the present invention is illustrated in FIG. 1 and as part of the cannula assembly 10 of the present invention, in FIG. 2. The piercing member 12 includes a tip 14, a shaft 16 and a retention means. Preferably of a general conical shape, tip 14 has a sharpened or spike point 18, a body portion 20 and a base 22. Body portion 20 is provided with at least one cutout, preferably two cutouts 24 and 26. The shaft 16 has a squared off portion 28 fitting within cutouts 24, 26 so that shaft 16 is integrally connected with and extending from tip 14. At least one channel, preferably two channels 30 and 32, are created by the fitment of squared portion 28 and cutouts 24, 26. The shaft 16 terminates at the opposing end in a taper surface 34. Opposing taper surface 34, retention means in the preferred embodiment includes a detent 36.

The preferred embodiment shown in FIG. 1 also includes an alignment means which is a series of corners 38, 40, 42, and 44 positioned at the termination of squared portion 28. From corners 38, 40, 42 and 44 the shaft conforms or transits in region 46 from the generally squared portion 28 into a generally cylindrical extension 48.

The cannula assembly 10 illustrated in FIG. 2, is designated generally by the reference numeral 10 and includes a blunt cannula 50 and piercing member 12. As described in pending applications, the cannula 50 includes a proximal end 52 defining an interior region 54 and may have a luer flange 56 for connection to a suitable mating engaging structure such as a syringe. A generally cylindrical mid-region 58 extends from the proximal end 52 and an end region 60 extends from the mid-region 58. This embodiment of the cannula 50 minimizes kick-back or recoil owing to the provisions of substantially cylindrical mid-region 58. This embodiment of the cannula 50 also increases withdrawal or tug resistance.

A generally cylindrical internal flow channel 62 extends through the end region 60 and mid-region 58 in communication with the interior region 64 of the proximal end region 52. The end region 60 is provided with a tapered surface 66 to minimize the insertion force.

The shaft 16 of piercing member 12 is slidably received within flow channel 62 of blunt cannula 50 through end region 60. When completely received within cannula 50, shaft 16 extends into interior region 54 of cannula 50 and base 22 contacts the distal blunt end 68 of end region 60. In this embodiment, the detent 36 is positioned against the stepped wall 70 between proximal end 52 and midregion 58 to prevent the inadvertent disengagement of piercing member 12 and cannula 50. Corners 38, 40, 42 and 44 align or center piercing member 12 within flow channel 62. Since the outer diameter of shaft 16 is slightly less than the interior diameter of flow channel 62, a void 72 is created between shaft 16 and interior surfaces of end region 60 and mid-region 58. Void 72 permits fluid and air flow through flow channel 62 despite the presence of shaft 16.

Figure 3C:
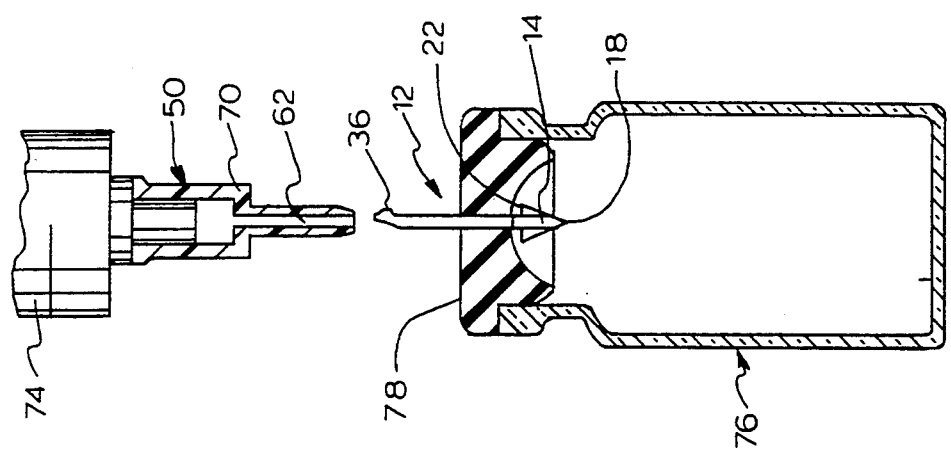
FIGS. 3A, 3B and 3C are cross-sectional views illustrating the operation of the cannula assembly.
Figure 3B:
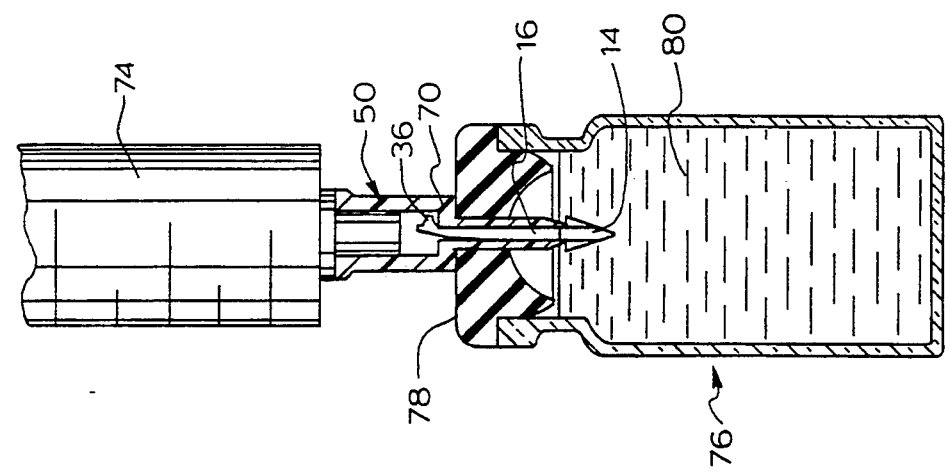
Figure 3A:
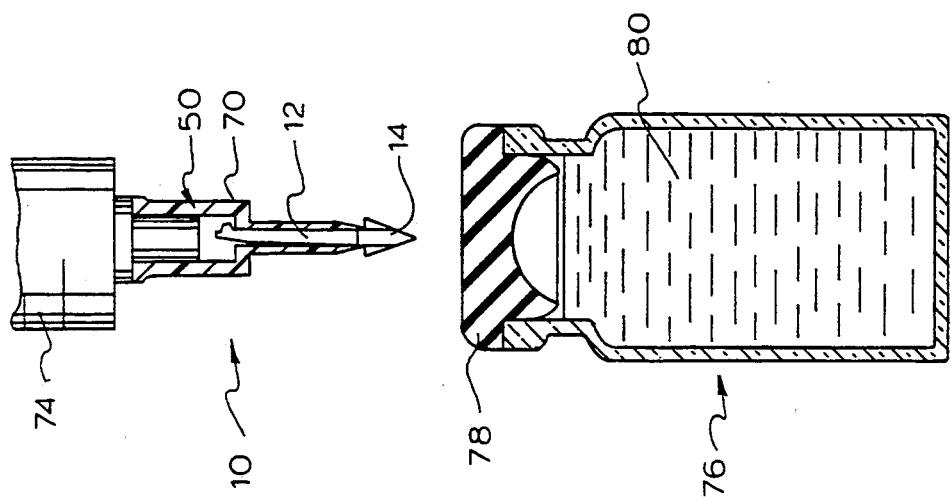

This embodiment of cannula assembly 10 can be packaged as a single-use medical device in a sterile blister pack and utilize a standard tip protector cover over cannula assembly 10. As best illustrated in FIGS. 3A-3C, Cannula assembly 10 is removed from the blister pack and releasably connected to a fluid flow member or receiver such as a syringe 74 of known construction. Following drug package instructions, a standard single use drug vial 76 having a solid closure or stopper 78 is prepared. After removal of the tip protector, a volume of air can be drawn into or expelled from syringe 74, if required, without dislodging cannula assembly 10. The cannula assembly 10 connected with syringe 74 is then positioned at the center of stopper 78 and pressed firmly towards vial 76 so that piercing member 12 pierces through stopper 78. To reduce the insertion force required, tip 14 can be lubricated, for example, during the manufacturing process, with silicone.

As shown in FIG. 3B, cannula assembly 10 is inserted through stopper 78 until stepped wall 70 provides a positive stop to insertion by meeting the upper surface of either vial 76 and/or stopper 78. Complete insertion is achieved when tip 14 and the immediate portion of shaft 16 pass beyond stopper 78 and enter the vial chamber 80. In this example, the liquid held in vial chamber 80 can now be removed through cannula assembly 10 and into the syringe 74. Once the liquid has been removed from chamber 80, syringe 74 and cannula assembly 10 are withdrawn from vial 76. As cannula assembly 10 exits stopper 78, base 22 of tip 14 meets stopper 78 and prohibits the further withdrawal of piercing member 12. At this point of the withdrawal procedure, sufficient force is created to cause taper surface 34 to deflect, permitting detent 36 to slide over stepped wall 70 and through flow channel 62, thereby permitting the disengagement of piercing member 12 from cannula 50.

As illustrated in FIG. 3C, cannula 50 while still connected with syringe 74, is completely withdrawn from stopper 78. Piercing member 12 remains either in the vial chamber 80 or imbedded in stopper 78. The vial 76 with piercing member 12 can then be disposed of without the user having any further exposure to spike point 18 or piercing member 12. The syringe 74 with cannula 50 is now ready for insertion into an injection site or other closure having a pre-slit septum, for example as those disclosed in related pending applications.

Although the retention means of the preferred embodiment of the cannula assembly 10 has been described as a force fit between detent 36 and stepped wall 70, retention could be achieved when detent 36 remains in flow channel 62 of mid-region 58 causing the end of shaft 16 to flex and contact at least some portion of the inner surface or wall of mid-region 58. Retention could also be achieved through a spring-type action. Absent detent 36, a spring action retention means can be achieved through a naturally arced or curved shaped shaft with sufficient flexibility so that the shaft generally straightens upon insertion into flow channel of the cannula. When the base of tip contacts the vial stopper and causes the separation of the piercing member from the cannula, the shaft returns to its natural curved state.

Figure 4:
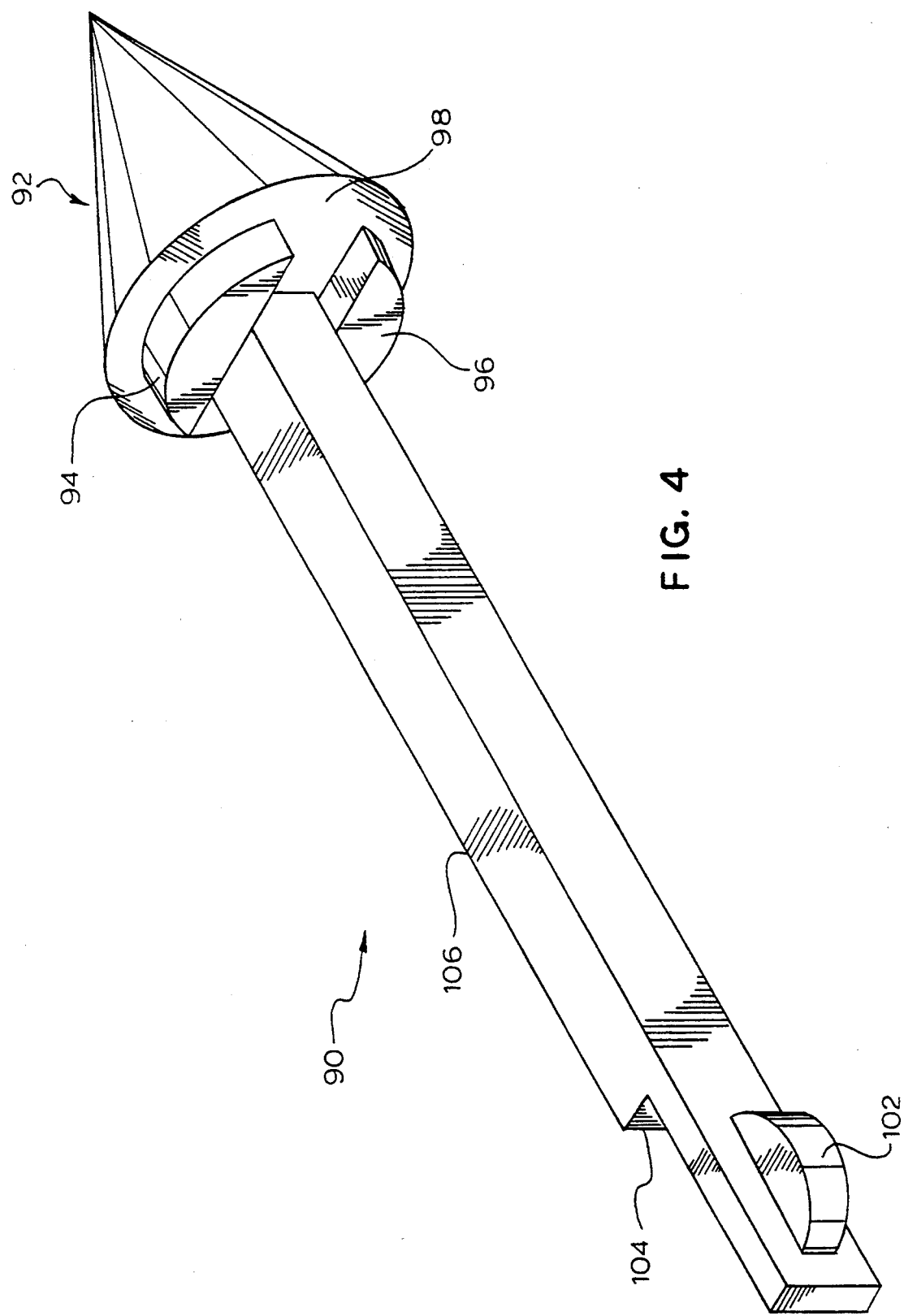
FIGS. 4, 5 and 6 are to be perspective views of alternative embodiments of the piercing device; and, FIGS. 7, 8 and 9 are cross-sectional views of alternative embodiments of the cannula assembly.
Figure 5:
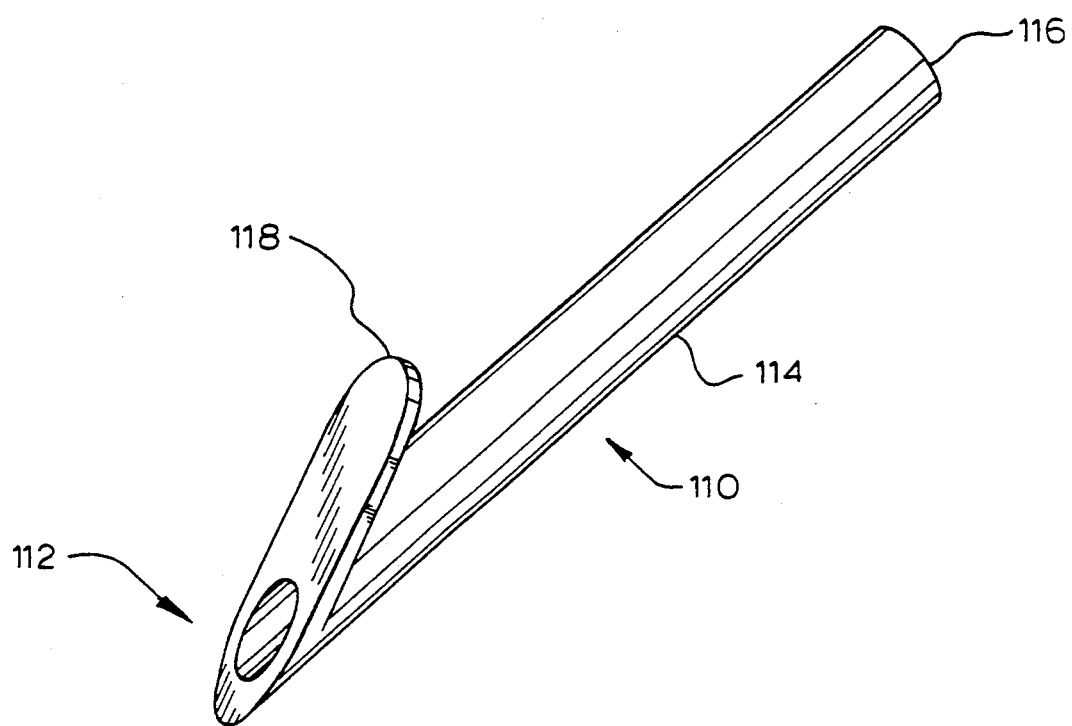
Figure 6:
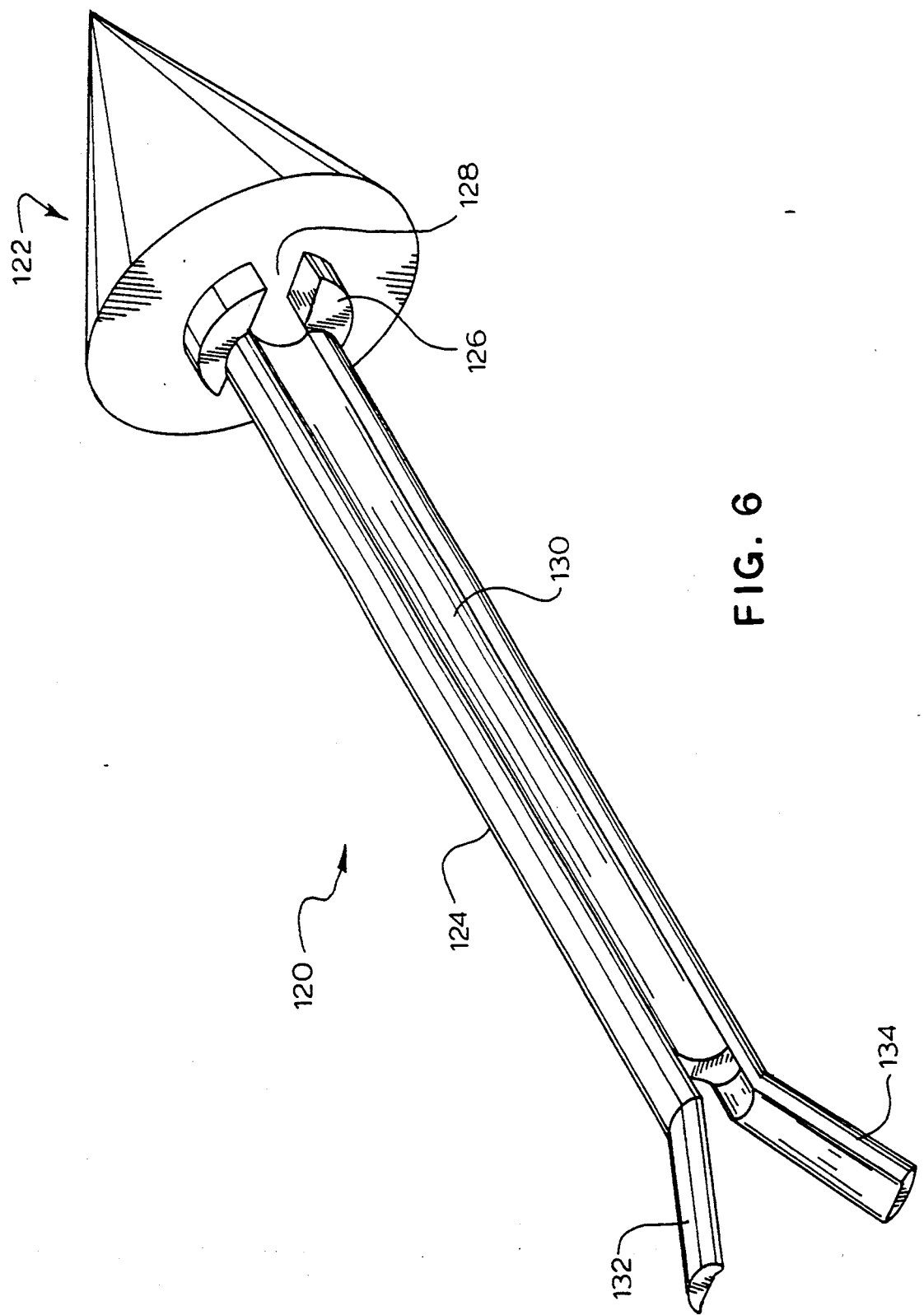

Further variations on piercing member are illustrated in FIGS. 4-6 with the following description highlighting some of the distinctions between the embodiments. Shown in FIG. 4, piercing member 90 includes a solid tip 92 with a pair of stand-offs 94 and 96 positioned on the base 98 of tip 92. Upon assembly of cannula 50 and piercing member 90, stand-offs 94, 96 rest against distal blunt end 68 of cannula 50. Stand-offs 94, 96 create a void 100 to permit fluid and air flow through the flow channel 62 of cannula 50. In addition, piercing member 90 is provided with a retention means including a detent 102 differing from the preferred detent 36 in shape. Detent 102 cooperates with a stepped portion 104 of the terminal end of shaft 106 in the appropriate retention through either force fit or a spring action, of piercing member 90 within cannula 50.

FIG. 5 illustrates a third embodiment of piercing member 110 differing in tip 112 being of a general arrowhead structure and shaft 114 although generally cylindrical in shape also having an outer diameter gradually decreasing through shaft 114 from the integral connection with tip 112 to the terminal end 116 of shaft 114. In this manner, piercing member 110 is force fit into flow channel 62 of cannula 50. The piercing member 110 will remain either in the vial chamber 80 or imbedded in stopper 78 upon withdrawal of cannula 50 as the base 118 of the arrowhead tip 112 does not permit withdrawal from stopper 78.

As can be appreciated, the force fit of piercing member 110 can also be achieved by reversing the variation of the outer diameter, that is increasing from integral connection with tip 112 to terminal end 116 of shaft 114. The force fit retention is achieved as long as interference occurs at some point along the shaft and the inner surface of cannula.

FIG. 6 also illustrates another embodiment of piercing member 120 differing in a solid tip 122 integrally connected with the shaft 124 at a thickened neck portion 126 of shaft 124. The neck portion 126 is of a sufficient thickness so as to provide a void 128 between distal blunt end 68 and tip 122. Running longitudinally through shaft 124, a groove 130 is formed to permit fluid flow along shaft 124. Rather than terminally end with a taper surface and detent, the subject piercing member 120 is provided with a pair of deflecting fingers 132, 134 which can be forcibly flexed inward or toward one another upon assembly of piercing member 120 and cannula 50. Upon insertion in flow channel 62, deflecting fingers 132, 134 will naturally flex outwardly once they pass stepped wall 70 of cannula 50, thereby functioning similarly to tapered surface 34 and detent 36. Further, if deflecting fingers 132, 134 do not pass stepped wall 70, but remain in flow channel 62, deflecting fingers 132, 134 will achieve retention of piercing member 120 in cannula 50 through a spring action.

Figure 7:
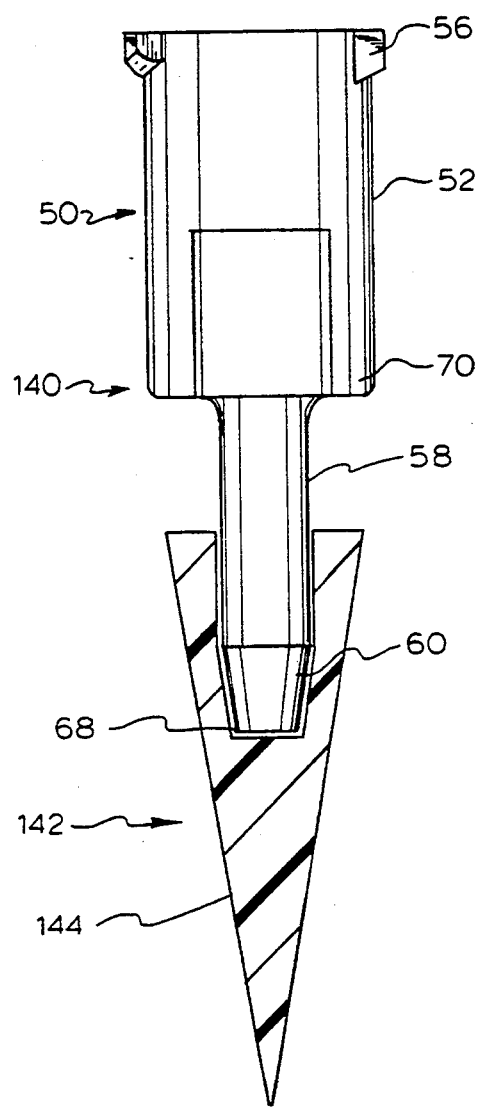
Figure 9:
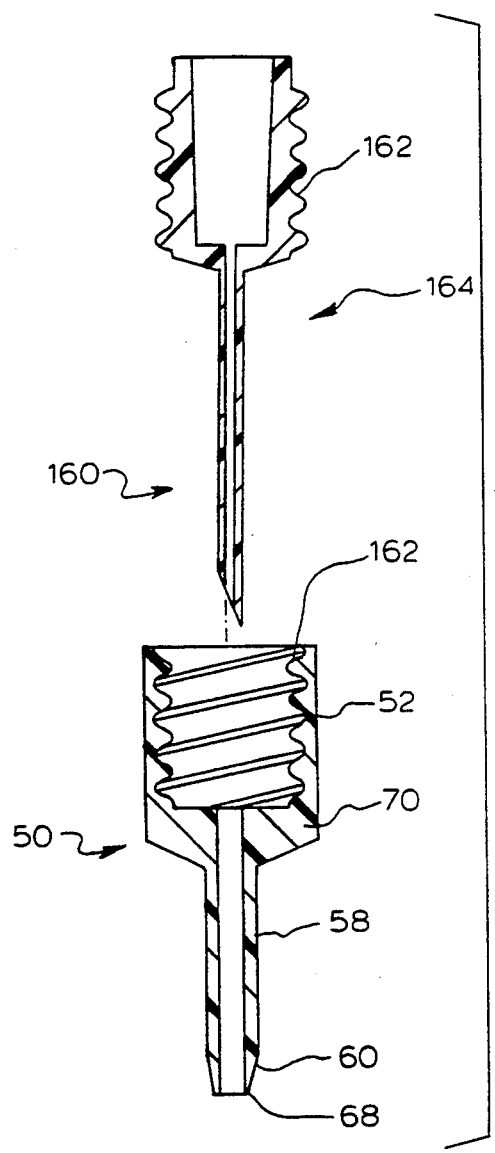
Figure 8:
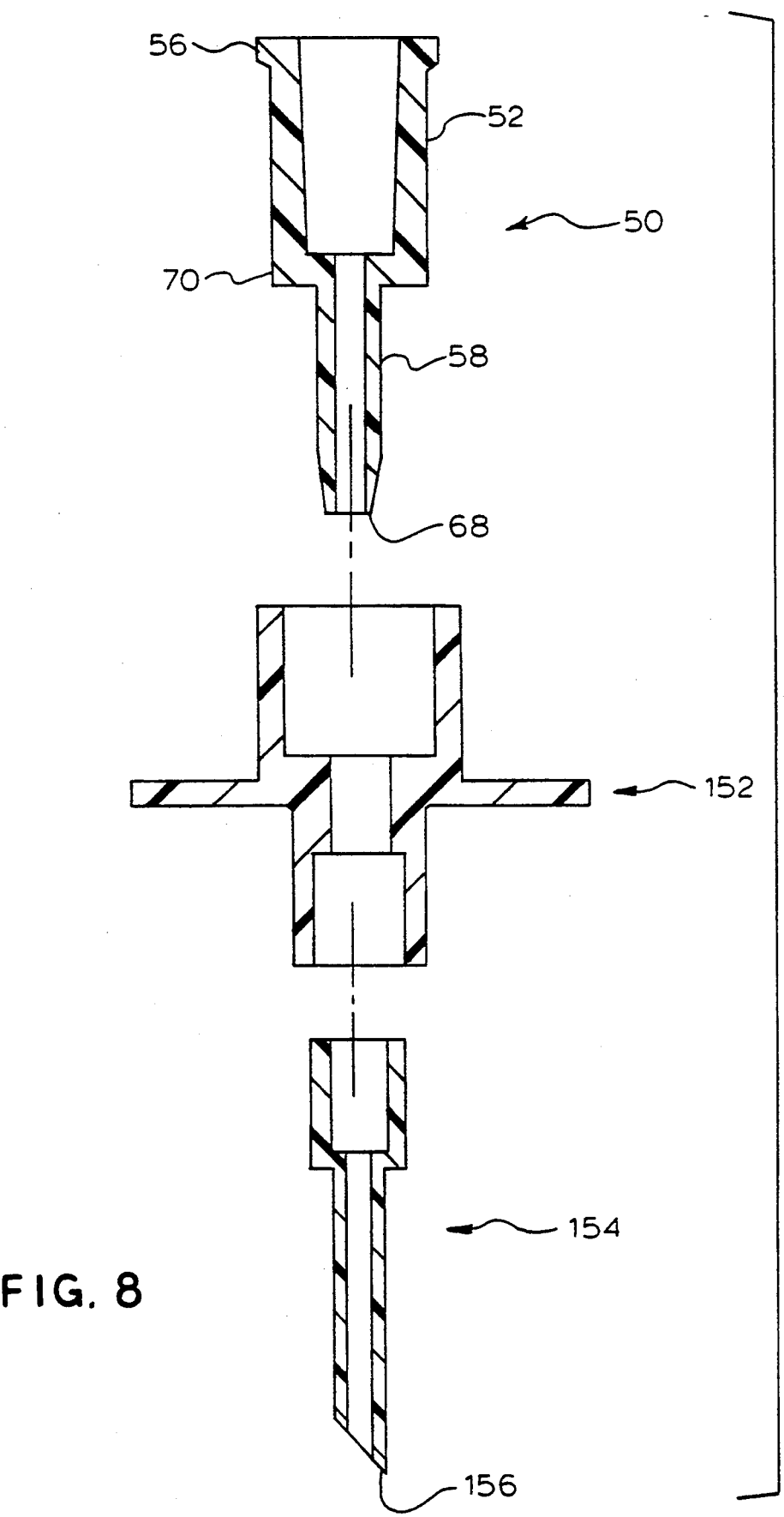

Additional embodiments of the cannula assembly are illustrated in FIGS. 7, 8 and 9. The cannula assembly 140 shown in FIG. 7 includes a piercing member 142 having a tip 144 of an arrowhead shape which is friction fit over distal blunt end 68 of cannula 50 as opposed to a force fit or spring action retention within flow channel of cannula. Upon insertion and withdrawal of assembly 140, piercing member 142 parts from cannula 50 and remains in the drug vial chamber 80.

Although shown in FIG. 7 as having a generally solid conical shape, piercing member 142 could be provided with a plurality of flexible fingers, creating an umbrella-type structure. Due to their flexibility, upon insertion of such a cannula assembly into a drug vial stopper, the fingers would fold in or close as an umbrella-type structure and then relax in a partially opened state after complete insertion. Upon withdrawal of such an assembly, the flexible fingers would contact the underside of the stopper and fan out, causing the separation of the piercing member from the cannula, thereby prohibiting the removal of such a piercing member from the vial.

FIGS. 8 and 9 illustrate cannula assemblies 150 and 160 which utilize a positive connecting means such as a flexible coupling member 152 in FIG. 8 or a threaded lock 162 as in FIG. 9, to permit appropriate retention and separation between piercing members 154 or 164 and cannulae 50. The cannula assembly 150 illustrated in FIG. 8 further provides an assembly which permanently incorporates the piercing member 154 inside of the cannula 50 and prohibits the piercing member 154 from becoming imbedded in the vial stopper 78 upon withdrawal of the assembly 150. Rather, the piercing member 154 is retracted within the cannula 50 through a twist motion so that the spike point 156 of the piercing member 154 is retracted into and contained within flow channel 62 of cannula 50. After administration of the fluid from the syringe, the entire cannula assembly 150 can then be disposed of without the user coming in contact with the spike point 156 of the piercing member 154.

From the description of these various embodiments, it is clear that numerous modifications to the cannula assembly come to mind without significantly departing from the spirit of the invention, and the scope of protection is only limited by the scope of the accompanying claims.

What we claim is:

1. A cannula assembly adapted to pierce a solid closure or stopper comprising:
   a blunt cannula having
      a proximal end with an interior region and terminating with a luer flange for connection to an engaging structure,
      a generally cylindrical mid-region extending from the proximal end,
      an end region extending from the mid-region terminating in a blunt distal end and having a tapered outer surface,
      an internal flow channel extending through the end region and mid-region to communicate with the interior region of the proximal end region,
      an aperture at the outermost end of the cannula and in fluid communication with the internal flow channel,
   a piercing member in communication with the flow channel and,
   means for providing an interference fit between the piercing member and the cannula.

2. The cannula assembly of claim 1 wherein the piercing member comprises a tip having a spike point, a body portion and a base.

3. The cannula assembly of claim 1 wherein the piercing member comprises a tip having a spike point, a body portion, a base and at least one channel longitudinally through the body portion.

4. The cannula assembly of claim 1 wherein the piercing member comprises a tip having a spike point, a body portion, a base and at least one channel longitudinally along the body portion.

5. The cannula assembly of claim 1 wherein the means for retention comprises a friction fit between the piercing member and the blunt distal end of the blunt cannula.

6. A cannula assembly adapted to pierce a solid closure or stopper comprising:
   a blunt cannula having
      a proximal end with an interior region and terminating with a luer flange for connection to a mating structure,
      a generally cylindrical mid-region extending from the proximal end,
      an end region extending from the mid-region terminating in a blunt distal end and having a tapered outer surface,
      an internal flow channel extending through the end region and mid-region to communicate with the interior region of the proximal end region,
      an aperture at the outermost end of the cannula and in fluid communication with the internal flow channel;
   a piercing member slidably cooperating with the flow channel, having
      a tip having a spike point, a body portion and a base,
      a shaft integral with and extending from the base of the tip; and,
   means for providing an interference fit between the piercing member and the cannula.

7. The cannula assembly of claim 6 wherein the body of the tip comprises a generally conical shape.

8. The cannula assembly of claim 6 wherein the tip comprises a generally solid conical shape with at least one cutout.

9. The cannula assembly of claim 6 wherein the shaft includes an alignment means having a squared portion integral with the tip which includes a series of corners opposing the tip which initiate a transition region forming a generally cylindrical extension.

10. The cannula assembly of claim 6 wherein the shaft includes an alignment means having a thickened neck portion integral with the base of the tip.

11. The cannula assembly of claim 6 wherein the shaft includes an outer diameter less than the inner diameter of the flow channel so that a void is created between the shaft and the cannula permitting fluid or air flow through the flow channel.

12. The cannula assembly of claim 6 wherein the shaft includes a thickened neck portion integrally connected to the base of the tip so that a void is created between the shaft and the cannula permitting fluid or air flow through the flow channel.

13. The cannula assembly of claim 6 wherein the means for retention comprises a tapered surface of a terminal end of the shaft opposing the integral connection with the base and a detent integral with terminal end and opposing the tapered surface.

14. A cannula assembly adapted to pierce a solid closure or stopper having a blunt cannula with a blunt distal end, a proximal end and a mid-region connecting the distal and proximal ends with a stepped wall segregating the mid-region and proximal end, an interior region throughout the mid-region and terminating at each end defining a flow channel and a piercing member slidably cooperating with the flow channel, the piercing member comprising:
 a tip having a spike point, a generally conically shaped body and a base with at least one cutout through the body and base,
 a shaft having a squared portion integral with and extending from the base of the tip, terminating in a series of corners, a transition region tapering from the corners into a generally cylindrical extension to a proximal end and,
 means for providing an interference fit between the piercing member and the cannula.

15. The piercing member of claim 14 wherein the piercing member cooperates with the flow channel by the shaft being slidably received within the flow channel so that the shaft extends into the proximal end of the cannula and the corners contact the distal end of the cannula.

16. The piercing member of claim 14 wherein the piercing member cooperates with the flow channel by the shaft being received within the flow channel so that the corners contact the distal end of the cannula.

17. The piercing member of claim 14 wherein the piercing member cooperates with the flow channel by the shaft being slidably received within the flow channel, thereby creating a void between the shaft and the interior surfaces of the distal end and mid-region of the cannula.

18. The piercing member of claim 14 wherein the means comprises a detent integral with the proximal end of the piercing member.

19. The piercing member of claim 14 wherein the means comprises a detent integral with the proximal end of the piercing member so that upon cooperation of the piercing member and the flow channel the detent is positioned against the stepped wall thereby preventing inadvertent disengagement of the piercing member and the cannula.

20. A method of effecting a transfer of fluid from a drug vial having a solid stopper closure to a receiver using a cannula assembly with a blunt cannula and a cooperating piercing member comprising the steps of:
 releasably connecting the cannula assembly to the receiver;
 positioning the connected cannula assembly at the center of the stopper and applying force for insertion of the assembly into and through the stopper;
 infusing fluid from the drug vial through the cannula assembly to the receiver; and,
 withdrawing the cannula assembly from the stopper so that the piercing member disengages from the cannula and the cannula is completely removed from the stopper.

21. The method of claim 20 including the step of drawing a volume of air into the receiver after connecting the cannula assembly to the receiver without dislodging the assembly from the receiver.

22. The method of claim 20 including the step of expelling a volume of air from the receiver into the drug vial after insertion of the cannula assembly through the stopper without dislodging the assembly from the receiver.

23. The method of claim 20 wherein the disengaging piercing member remains contained in the drug vial.

24. The method of claim 20 wherein the disengaged piercing member is imbedded in the stopper.

25. A cannula assembly adapted to pierce a solid closure comprising:
 a blunt cannula having a proximal end and a distal end, an interior and exterior surface, an aperture at the distal end, and a central channel through the cannula in fluid communication with the aperture, the cannula has a generally cylindrical mid-region, the exterior surface of the cannula tapers inwardly from the mid-region of the cannula toward the aperture;
 a piercing member having opposed first and second ends, the first end extends through the aperture inside the central channel to define a void to allow for the flow of liquid or air, the second end of the piercing member being adjacent the cannula distal end; and,
 means for providing an interference fit between the piercing member and the cannula.

26. The cannula assembly of claim 25 wherein the means for attaching the piercing member to the cannula includes:
 means at the first end of the piercing member for applying a first force against the cannula to prevent movement of the piercing member away from the cannula; and,
 means at the second end of the piercing member adapted for applying a second force greater than the first force against the closure to prevent retrograde motion of the piercing member toward the cannula.

27. The assembly of claim 26 wherein the piercing member first end extends inside the cannula channel and attaches to the interior surface of the cannula.

28. The assembly of claim 27 wherein the means for applying the first force is a detent at the first piercing member end.

29. The assembly of claim 28 wherein the detent has a trapezoidal shape having a flat apex and two opposed downwardly and outwardly sloping legs.

30. The assembly of claim 26 wherein the piercing member has an elongate shaft having first and second opposed ends, wherein the means for applying the second force includes an enlarged tip at the second shaft end.

31. The assembly of claim 30 wherein the tip is generally conically shaped.

32. The assembly of claim 31 wherein the tip has a portion removed to define a cut-out.

33. The assembly of claim 30 wherein an intermediate portion of the shaft has a square shaped cross section.

34. A cannula assembly adapted to pierce a solid closure or stopper comprising:
a blunt cannula having a proximal end with an interior region, a generally cylindrical mid-region extending from the proximal end, an end region extending from the mid-region terminating in a blunt distal end and having a tapered outer surface, an internal flow channel extending through the end region and mid-region to communicate with the interior region of the proximal end region;
a piercing member slidably cooperating with the flow channel, having a tip having a spike point, a body portion and a base, a shaft integral with and extending from the base of the tip, the shaft having a squared portion integral with the tip; and,
means for providing an interference fit between the piercing member and the cannula.

35. A cannula assembly adapted to pierce a solid closure or stopper comprising:
a blunt cannula having a proximal end with an interior region, a generally cylindrical mid-region extending from the proximal end, an end region extending from the mid-region terminating in a blunt distal end and having a tapered outer surface, an internal flow channel extending through the end region and mid-region to communicate with the interior region of the proximal end region;
a piercing member slidably cooperating with the flow channel, having a tip having a spike point, a body portion and a base, a shaft integral with and extending from the base of the tip, the shaft having a thickened neck portion integral with the base of the tip; and,
means for providing an interference fit between the piercing member and the cannula.

36. A cannula assembly adapted to pierce a solid closure or stopper comprising:
a blunt cannula having a proximal end with an interior region, a generally cylindrical mid-region extending from the proximal end, an end region extending from the mid-region terminating in a blunt distal end and having a tapered outer surface, an internal flow channel extending through the end region and mid-region to communicate with the interior region of the proximal end region;
a piercing member slidably cooperating with the flow channel, the piercing member having a tip having a spike point, a body portion and a base, a shaft integral with and extending from the base of the tip, the shaft having an outer diameter less than an inner diameter of the flow channel to define a void between the shaft and the channel to permit the flow of fluid or air through the void in the flow channel; and,
means for providing an interference fit between the piercing member and the cannula.

37. A cannula assembly adapted to pierce a solid closure or stopper comprising:
a blunt cannula having a proximal and distal end, a flow channel extending therewithin, and an aperture in fluid communication with the flow channel;
a piercing member having a tip and a shaft extending from the tip, the shaft extends inside the flow channel to define a void to allow for the passage of fluid or air through the flow channel; and,
means for providing an interference fit between the piercing member and the cannula.

* * * * *